US00PP21396P3

(12) United States Plant Patent
Bourne

(10) Patent No.: US PP21,396 P3
(45) Date of Patent: Oct. 19, 2010

(54) ***DIANTHUS* PLANT NAMED 'WP08 ULR03'**

(50) Latin Name: *Dianthus×hybrida*
Varietal Denomination: WP08 ULR03

(76) Inventor: Carolyn Grace Bourne, Houndspool, Ashcombe Road, Dawlish, Devon (GB) EX7 0QP ( * ) Notice: Subject to any disclaimer, the term of this patent is extended or adjusted under 35 U.S.C. 154(b) by 0 days.

(21) Appl. No.: 12/456,955

(22) Filed: Jun. 24, 2009

(65) Prior Publication Data

US 2010/0058506 P1 Mar. 4, 2010

(51) Int. Cl.
*A01H 5/00* (2006.01)

(52) U.S. Cl. ..... Plt./281

(58) Field of Classification Search ..... Plt./281
See application file for complete search history.

*Primary Examiner*—Annette H Para

(57) ABSTRACT

A new cultivar of *Dianthus* plant named 'WP08 ULR03' whose flowers are fully double and bright vibrant pink in color, and which are strongly pleasantly fragrant. In combination these traits set 'WP08 ULR03' apart from all other existing varieties of *Dianthus* known to the inventor.

2 Drawing Sheets

Genus: *Dianthus.*
Species: ×*hybrida.*
Denomination: 'WP08 ULR03'.

BACKGROUND OF THE INVENTION

This application claims the benefit of priority under 35 U.S.C. 119(f) of the application for a grant of European Community Plant Breeders Rights which was filed for the instant plant variety on Jun. 30, 2008, Application Number 2008/1510.

The present invention relates to a new and distinct cultivar of hardy garden pink or carnation which is grown for use as a flowering plant for pots and containers and for planting in the garden or landscape. The new cultivar is known botanically as *Dianthus×hybrida* and will be referred to hereinafter by the cultivar name 'WP08 ULR03'.

'WP08 ULR03' is a complex hybrid plant that is the product of a breeding program started by the inventor in 1985. The breeding program is conducted in a cultivated area of Houndspool, Dawlish, Devon, United Kingdom. The inventor selected 'WP08 ULR03' in 2003 for its flowers that are fully double and bright vibrant pink in color, and which are strongly pleasantly fragrant.

'WP08 ULR03' resulted from the controlled pollination between two unreleased and unpatented varieties raised by the inventor, namely *Dianthus* code number ASH10 as female parent plant and *Dianthus* code number 00.68 as male parent plant.

'WP08 ULR03' is distinguishable from the female parent as follows: The female parent has semi-double white flowers.

'WP08 ULR03' is distinguishable from the male parent as follows: The male parent is taller in height and has larger double orange flowers.

The variety of *Dianthus* which is considered by the inventor to most closely resemble 'WP08 ULR03' is the inventor's variety *Dianthus* 'Devon Flavia' (U.S. Plant Pat. No. 15,903). 'WP08 ULR03' is distinguishable from this variety as follows: The flowers of 'Devon Flavia' are bi-colored pink with reddish purple "eye" and are semi double.

Asexual reproduction of the new cultivar was first accomplished by the inventor in 2003 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP08 ULR03'. These traits in combination distinguish this cultivar from all other commercial varieties known to the inventor. 'WP08 ULR03' has not been tested under all possible conditions and phenotypic differences may be observed with variations in environmental, climatic and cultural conditions, however, without any variance in genotype.

1. *Dianthus* 'WP08 ULR03' exhibits a compact habit.
2. *Dianthus* 'WP08 ULR03' blooms profusely from April until October.
3. The flowers of *Dianthus* 'WP08 ULR03' are fully double and are bright vibrant pink in color.
4. *Dianthus* 'WP08 ULR03' is strongly pleasantly fragrant.
5. *Dianthus* 'WP08 ULR03' exhibits grey-green foliage.
6. After nine months of growth, the height of the foliage mound of *Dianthus* 'WP08 ULR03' is 19 cm to 22 cm; the width is 11 cm to 14 cm.
7. *Dianthus* 'WP08 ULR03' is perennial and is hardy to −15° C.

BRIEF DESCRIPTION OF THE DRAWINGS

The accompanying color drawings illustrate the overall appearance of the new *Dianthus* variety 'WP08 ULR03' showing colors as true as it is reasonably possible to obtain in colored reproductions of this type. Colors in the drawings may differ from the color values cited in the detailed botanical description, which accurately describe the actual colors of the new variety 'WP08 ULR03'.

The drawing labeled as FIG. 1 depicts an entire flowering plant.

Figure 1:
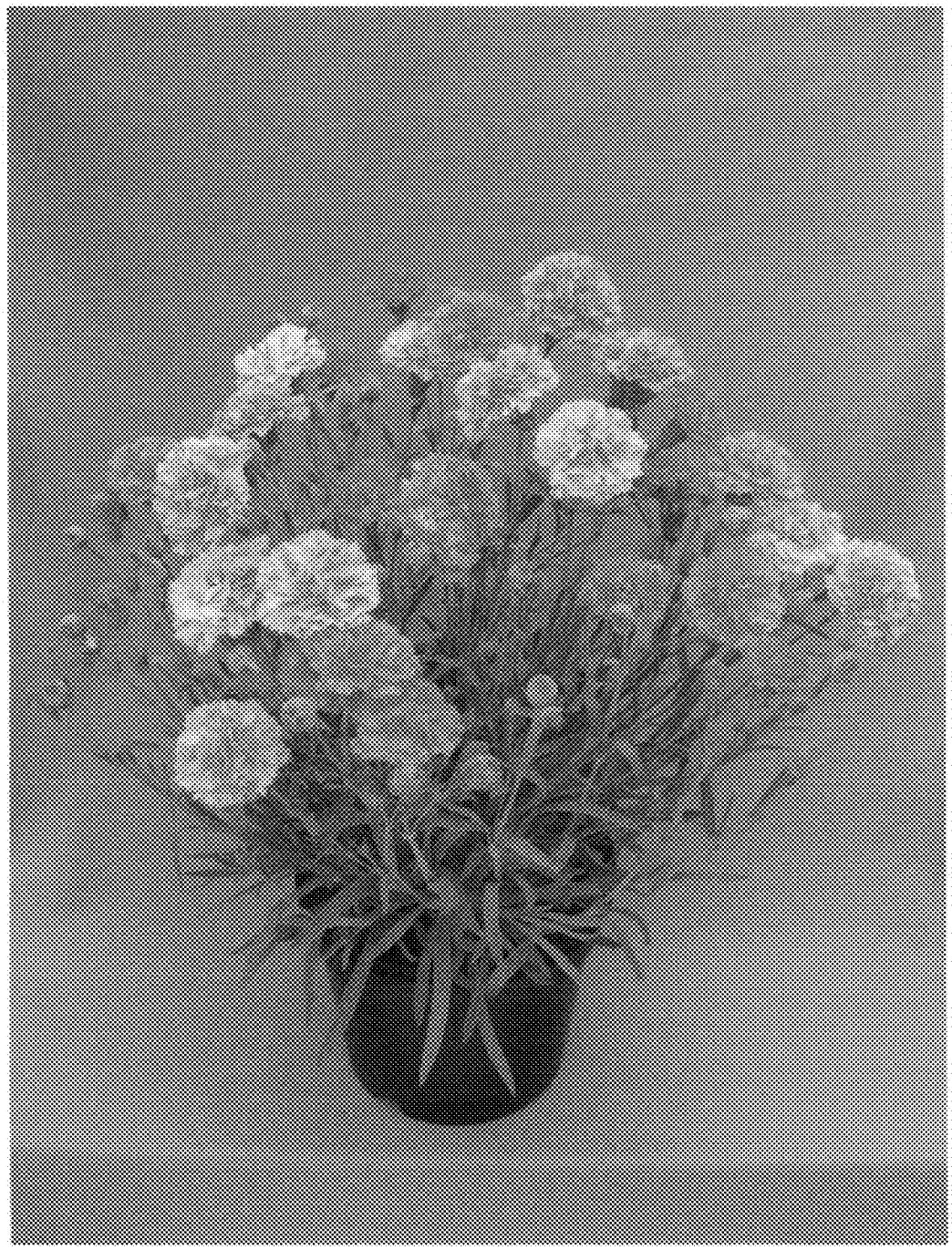
Figure 2:
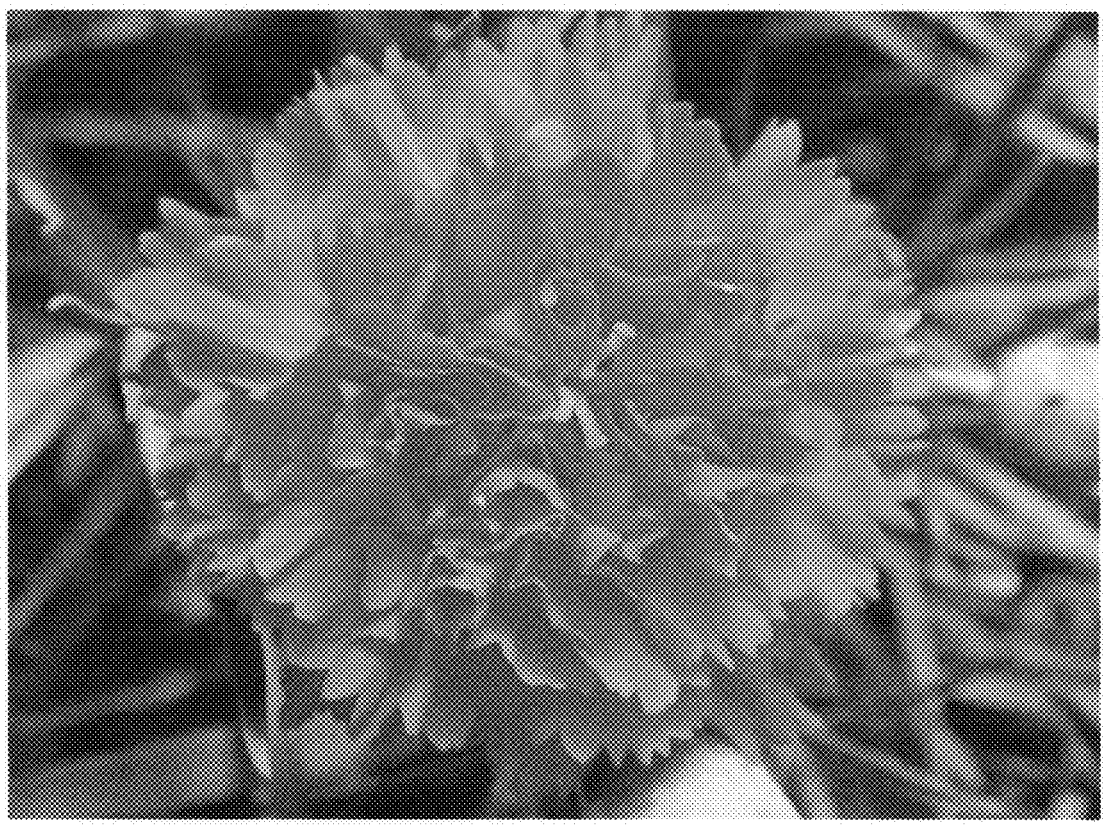

The drawing labeled as FIG. 2 depicts a close-up view of the flower.

All drawings were made of 9 months old plants which have been grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP08 ULR03'. Data was collected in spring from 1.5-liter container plants in spring, and grown indoors in Devon, United Kingdom. The color determinations are in accordance with the 2007 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification:
- *Family.*—Caryophyllaceae.
- *Genus.*—*Dianthus.*
- *Species.*—×*allwoodii* .
- *Denomination.*—'WP08 ULR03'.

Parentage: A complex *Dianthus* hybrid whose immediate parents are unreleased hybrids from the inventor's breeding program, identified as follows:
- *Male parent.*—Selection 00.68.
- *Female parent.*—Selection ASH10.

Plant type: Flowering perennial.

Use of plant: As a flowering plant in containers, window boxes, planters, pots and the garden.

Bloom period: April-October in Devon.

Plant habit: A compact mound with many branches and upright stems.

Height of plant: 19 to 22 cm after 9 months.

Width of plant: 11 to 14 cm after 9 months.

Hardiness: At least to minus 15 Centigrade.

Type: Perennial herb.

Root system: Many fibrous roots.

Propagation method: By vegetative stem cuttings.

Cultural requirements: Grow in full sun, in well drained and moderately fertile soil, keep well fertilized and watered.

Diseases and pests: No particular resistance or susceptibility to *Dianthus* diseases and pests are known to the inventor.

Time to root cuttings: 5 weeks is required to produce roots on a vegetative cutting.

Temperature for rooting: A minimum of 15° C. air temperature and 21° C. base temperature at root level is required to produce roots on the cuttings.

Facilities for rooting: A mist propagation unit is required for satisfactory rooting of cuttings.

Crop time: 3 months starting in the Spring and 6 months starting in the Fall.

Plant stem:
- *Shape.*—Cylindrical.
- *Dimensions.*—Height: 9 to 11 cm. Diameter: 4 to 5 mm.
- *Surface.*—Glabrous and glaucous.
- *Color.*—145C to 145D.
- *Branching.*—Numerous shoots from the axils of the lower leaves.

Internode length (between nodes): 6 to 8 mm.

Leaf:
- *Type.*—Evergreen.
- *Shape.*—Linear, straight.
- *Division.*—Simple.
- *Apex.*—Acute.
- *Base.*—Decurrent.
- *Venation.*—Faintly visible.
- *Margins.*—Entire.
- *Arrangement.*—Opposite and spiraling on stem.
- *Attachment.*—Sheathing.
- *Surface adaxial.*—Glaucous.
- *Surface abaxial.*—Glaucous.
- *Fragrance.*—Absent.
- *Dimensions.*—Length: 55 to 75 mm. Width: 4 to 5 mm.
- *Color adaxial surface.*—N138B to N138C.
- *Color abaxial surface.*—N138B to N138C.

Inflorescence:
- *Flower stem dimension.*—Length: 17 to 20 cm. Width: 3 mm. Stem strength: Erect. Color: 122A to 122C. Inflorescence: Cymose.
- *Type.*—Salviform, symmetrical.
- *Development.*—Singly, in sequence from the uppermost bud.

Bud:
- *Color.*—139C towards apex, 139D towards base.
- *Dimensions.*—13 cm in length, 10 cm in diameter.
- *Shape.*—Ovoid; apex acute until fully swollen and ready to open, then rounded.

Flowers:
- *Number.*—3 to 6 per stem.
- *Dimensions.*—Length including calyx: 30 to 33 mm. Diameter: 38 to 40 mm.
- *Flower shape.*—Circular.
- *Flower profile.*—Concave to convex.
- *Lastingness.*—10 days at 20° C., on the plant.
- *Fragrance.*—Medium.
- *Flowering period.*—April to October.

Corolla:
- *Shape* (*upper part of corolla*).—Convex.
- *Shape* (*lower part of corolla*).—Concave.
- *Petal arrangement.*—Persistent, double, overlapping.
- *Petal margin.*—Crenate-dentate.
- *Indentation.*—0.5 to 2 mm deep.
- *Petal texture.*—Soft.
- *Flower type.*—Double.
- *Petal number.*—30 to 35 petals normally develop with up to 15 additional petaloid stamens.
- *Petal dimension.*—Length: 31 to 33 mm. Width: 18 to 20 mm.
- *Color pattern.*—Self, bright pink.
- *Color of upper surface.*—Ground color of blade: 58B-58C when fresh, fading to N57D. Color of middle of strap: 145C. Color of base of strap: 145D.
- *Color of lower surface.*—Ground color of blade: 58B. Color of middle of strap: 145C. Color of base of strap: 145D.
- *Petal shape.*—Obdeltoid.
- *Petal surface.*—Glabrous, undulating.

Calyx:
- *Shape.*—Cylindrical to campanulate.
- *Longitudinal profile.*—Convex.
- *Dimensions.*—Length: 18 to 20 mm. Diameter: 12 mm.

*Sepals.*—Fused.
*Sepals number.*—5.
*Sepals color.*—138A.
*Anthocyanin.*—Present, edges of lobes.
*Splitting.*—Yes.

Epicalyx:
*Bracts number.*—1 pair of 2.
*Shape of outer lobe.*—Acute.
*Dimensions.*—Width: 5 mm. Length: 11 mm.
*Color.*—189A to N138A.
*Anthocyanin.*—Not present.

Bracteoles:
*Number.*—1 pair of 2.
*Dimensions.*—Width: 11 mm, Length: 8 to 10 mm.
*Color.*—189A to N138A.
*Anthocyanin.*—Not present.

Reproductive organs:
*Stamens.*—Number: about 10 but highly deformed or tiny or petaloid. Color of filaments: None evident.
*Anthers.*—None evident.
*Pollen.*—None evident.
*Style.*—Number: 2 to 3. Color: White. Dimensions: (style and stigma, at maturity).
*Dimensions.*—Length: 20 to 22 mm. Width: 0.5 mm.
*Stigma.*—Number: 2 to 3 (only one stigma per style). Shape, Attachment: Linear, runs along length of style rather than located at terminal of style. Color: N66C. Dimensions: 2 to 3 mm above the flower at maturity.
*Ovary.*—Position: Superior. Dimensions: Length: 9 to 10 mm; Diameter: 5 to 6 mm. Shape: Spindled but heavily deformed when the flower ages, due to development of a third style within the ovary. Color upper: 145A. Color lower: 145C.
*Seed.*—Not observed.

The invention claimed is:

1. A new and distinct cultivar of *Dianthus* plant named 'WP08 ULR03' as described and illustrated herein.

* * * * *